United States Patent
Sanghavi

(10) Patent No.: US 10,577,587 B2
(45) Date of Patent: Mar. 3, 2020

(54) METHOD OF INDUCING BONE FORMATION BY EX-VIVO OSTEOBLAST CULTURING FOR IMPLANTATION

(71) Applicant: REGROW BIOSCIENCES PRIVATE LIMITED, Mumbai (IN)

(72) Inventor: Satyen Sanghavi, Mumbai (IN)

(73) Assignee: REGROW BIOSCIENCES PRIVATE LIMITED, Mumbai, Maharashtra (IN)

( * ) Notice: Subject to any disclaimer, the term of this patent is extended or adjusted under 35 U.S.C. 154(b) by 193 days.

(21) Appl. No.: 15/512,798

(22) PCT Filed: Jul. 8, 2015

(86) PCT No.: PCT/IN2015/000277
§ 371 (c)(1),
(2) Date: Mar. 20, 2017

(87) PCT Pub. No.: WO2016/042572
PCT Pub. Date: Mar. 24, 2016

(65) Prior Publication Data
US 2017/0292114 A1    Oct. 12, 2017

(30) Foreign Application Priority Data
Sep. 19, 2014 (IN) .......................... 3005/MUM/2014

(51) Int. Cl.
| | |
|---|---|
| *C12N 5/077* | (2010.01) |
| *A61K 35/32* | (2015.01) |
| *A61L 27/02* | (2006.01) |
| *A61L 27/38* | (2006.01) |
| *A61L 27/54* | (2006.01) |

(52) U.S. Cl.
CPC ............ *C12N 5/0654* (2013.01); *A61K 35/32* (2013.01); *A61L 27/02* (2013.01); *A61L 27/3821* (2013.01); *A61L 27/3847* (2013.01); *A61L 27/54* (2013.01); *A61L 2430/02* (2013.01); *C12N 2500/00* (2013.01); *C12N 2500/02* (2013.01); *C12N 2506/1353* (2013.01)

(58) Field of Classification Search
None
See application file for complete search history.

(56) References Cited

FOREIGN PATENT DOCUMENTS

| | | |
|---|---|---|
| CN | 107075477 A | 8/2017 |
| NO | 2008035832 A1 | 3/2008 |

OTHER PUBLICATIONS

Min et al. Eur Spine J. vol. 19. pp. 1755-1759 (Year: 2010).*
Min et al., "Proliferation and osteblastic differentiation of bone marrow stem cells: comparison of vertebral body and iliac crest", Eur Spine J., 19: pp. 1753-1760, 2010.
Behera et al., "Casein hydrolysates enhance osteoblast proliferation and differentiation in mouse bone marrow culture", Food Bioscience, pp. 24-30, 2013.
Tsai et al., "Encapsulation and Growth Characteristics of Three Different cells in Alginate Gel Beads Containing Reconstituted Collagen Fibers", Biomedical Engineering Applications, Basis & Communications, vol. 18 No. 2, Apr. 2006.
Examination Report dated Feb. 21, 2019 in IN 3005/MUM/2014.
Written Opinion dated Dec. 4, 2017 in SG Application No. 11201702189S.
Written Opinion dated Mar. 6, 2019 in SG Application No. 11201702189S.
Int'l Preliminary Report on Patentability dated Mar. 21, 2017 in Int'l Application No. PCT/IN2015/000277.
Int'l Search Report and Written Opinion dated Feb. 2, 2016 in Inn Application No. PCT/IN2015/000277.

* cited by examiner

*Primary Examiner* — Blaine Lankford
(74) *Attorney, Agent, or Firm* — Panitch Schwarze Belisario & Nadel LLP

(57) ABSTRACT

An ex-vivo culturing method of osteoblasts for implantation, comprising a culturing of adult live osteoblasts as an ex-vivo procedure. The ex-vivo culture, which leads to the formation of the active substance, further comprises the steps of isolation of osteo-progenitor cells, differentiation of osteo-progenitor cells in to osteoblasts, expansion culture, cell culture harvest and wash followed by filling and packaging. This method is instrumental in accelerating the process of bone formation.

12 Claims, 9 Drawing Sheets

METHOD OF INDUCING BONE FORMATION BY EX-VIVO OSTEOBLAST CULTURING FOR IMPLANTATION

CROSS REFERENCE TO RELATED APPLICATIONS

This application is a national phase application under 35 U.S.C. § 371 of International application Ser. No. PCT/IN2015/000277, filed on Jul. 8, 2015, which claims priority to Indian Patent Application No. 3005/MUM/2014, filed on Sep. 19, 2014; the disclosures of all of which are hereby incorporated by reference in their entirety.

FIELD OF INVENTION

The present invention relates to a method of inducing bone formation, particularly by osteoblast implantation.

BACKGROUND OF INVENTION

Osteoblasts are known to be large cells in control of the synthesis and mineralization of bone formation and the subsequent remodeling of the same. The process of bone formation from osteoblasts is known as osteogenesis and involves three basic steps: (a) Synthesis of extracellular organic matrix (osteoid), (b) Matrix mineralization leading to the formation of bone, (c) Remodeling of bone by the process of resorption and reformation. Bone remodeling is a continuing process of synthesis and destruction that gives bone its mature structure and maintains the normal structure of bone. Now, destruction, or resorption of bone occurs by virtue of large cells called osteoclasts.

The conventional methods used for replacement of defect bones in bone associated diseases or during circumstances of new bone formation due to breakage or injury, are numerous. Depending on the case, certain scenarios can prove to be very challenging, especially the realignment of the bone.

Autologous bone graft of various types is available, which provide good mechanical and biological properties but factors like donor site morbidity, molding challenges, limited operative time for graft harvest and the limited volume in term of quantity available is a great concern. Again, allograft, which involves the transplant of a tissue, is one where the donor is of a different genetic makeup. Although allograft mitigates a few issues associated with autologous bone graft as there is no donor site morbidity and there is no limitation with respect to the quantity, few other problems are involved, which could be the sterilization process which weakens the bone rejection reactions due to a different genetic make-up or the graft may transmit infections such as hepatitis and HIV/AIDS.

Bone generation by virtue of growth factors such as BMPs (Bone morphogenic proteins) which is yet another method wherein the quantitative replacement of defective bone is considerably less to provide predictable results.

Therefore, the above-mentioned problems associated with the existing methods for replacement of defect bones need to be alleviated.

OBJECTIVES OF THE INVENTION

1. It is an object of the invention to induce bone formation using osteoblast cells.
2. It is another object of the invention to provide a method of mimicking natural bone formation, which delivers a highly-accelerated process as compared to already existing methods.
3. It is another object of the invention to provide a minimally invasive method and a time saving process as opposed to erstwhile known methods.
4. It is a further object of the invention to prevent donor site morbidity and provide a considerable volume of osteoblasts for bone formation.

SUMMARY OF THE INVENTION

The present invention addresses the existing problems associated with methods of inducing bone formation and provides an implantation method comprising an ex-vivo osteoblast culturing. Again, ex-vivo culturing can be defined as culturing in the external environment without alteration in the natural conditions and parameters. The ex-vivo culture, which leads to the formation of the active substance to be injected at the site of bone formation, further comprises the steps of isolation of osteo-progenitor cells, differentiation of osteo-progenitor cells in to osteoblasts, expansion culture, cell culture harvest and wash and filling and packaging. This invention particularly accelerates the bone formation process apart from being a minimally invasive method.

DETAILED DESCRIPTION OF THE INVENTION

Figure 1:
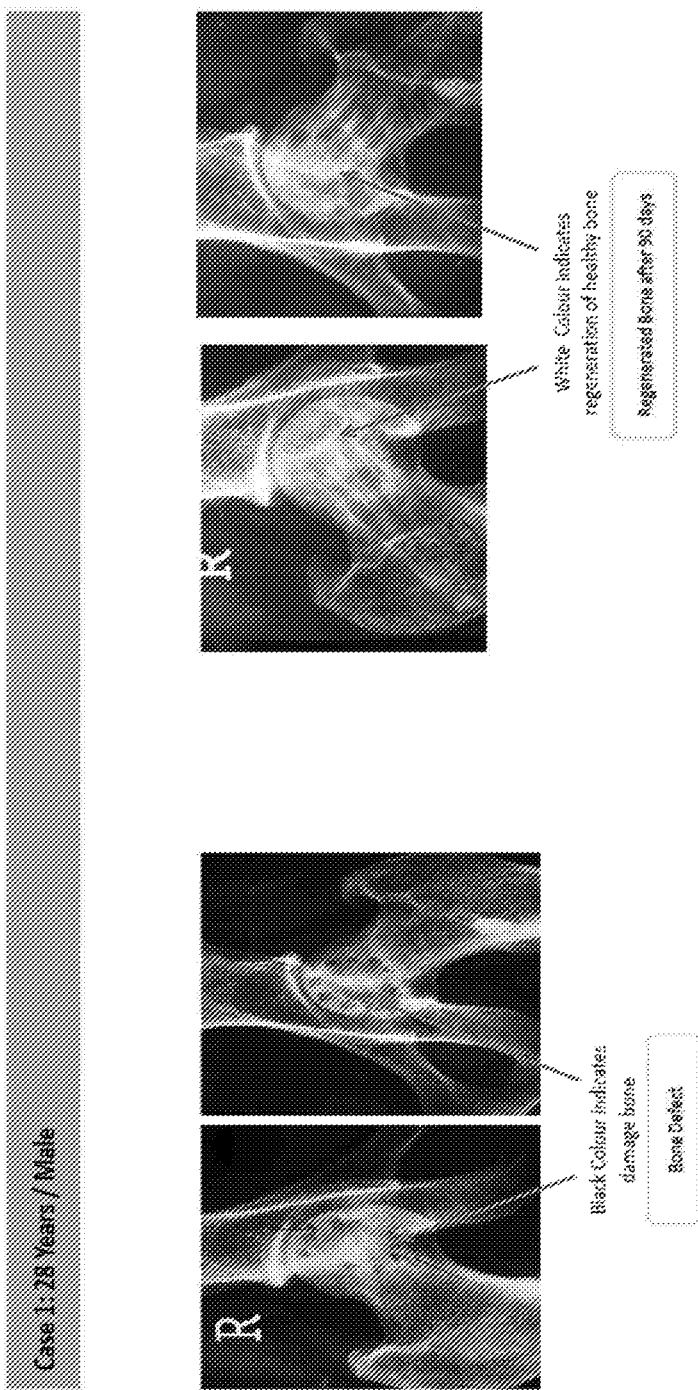
FIG. 1 is a radiological report wherein bone formation was observed 90 days after ex-vivo cultured osteoblasts were injected in a 28 year old patient in both the hip joints.

The present invention relates to a method of inducing bone formation by osteoblast implantation in the area of defect or a condition, which requires the same.

This inventive method, which is an osteoblast implantation method, is broadly constructed in a way that the method comprises steps for inducing bone formation.

Therefore, the broad steps involved in osteoblast implantation is an ex-vivo culture of live osteoblasts. Furthermore, in the following description the steps are described in detail:

The ex-vivo culturing follows the harvesting of bone marrow cells from a subject. Harvesting involves as the name suggests harvesting of bone marrow from the posterior-superior iliac crest or sternum of the Subject. Furthermore, the subject there is the receiver of the induced bone formation.

In order for the ex-vivo culture to be carried out, a biopsy kit needs to be shipped out of the place where the harvest was conducted. The biopsy kit is preconditioned prior to shipment and is transported under strict monitoring of temperature between the ranges of 2-8 degrees Celsius during transport. In addition, it has to be ensured that the collected bone marrow is aseptically transferred into sterile biopsy collection medium.

The ex-vivo osteoblast culturing, involves the formation of the active substance. Active substance can be defined as the substance, which is injected at the site of induced bone formation. The process which leads to the formation of the active substance further comprises the steps of:

Isolation of osteo-progenitor cells, differentiation of osteo-progenitor cells in to osteoblasts, expansion culture, cell culture harvest, washing and filling, characterised with Bone Alkaline Phosphatase and Collagenase Type I (CD 44$^+$ and/or CD151$^+$) cell surface markers, filled in sterile vials, sealed effectively under aseptic conditions, transported at 2 to 8 degrees Celsius and used as active substance within 72 hours from date of manufacture.

As mentioned above, the ex-vivo culturing starts with the isolation of osteo-progenitor cells. Osteo-progenitor cells are mesenchymal cells that differentiate into an osteoblast as collagen is secreted in the process to harden the bone structure. The rate of differentiation of bone marrow cells in to osteo-progenitor may be controlled by virtue of endothelial cells. Ideally, the osteo-progenitor cells should be maintained at a pre-osteoblastic stage at the site of inducing of bone formation thereby avoiding mineral deposition within the vessel. After the transfer from the vessels to the site of induction rapid differentiation of mature osteoblasts should occur.

In accordance with the invention, the isolation procedure in day one involves the collection of bone marrow with the biopsy collection medium in centrifuge tubes. The biopsy collection medium containing biopsy is checked with respect to sterility, cell viability, cell count, cell characterization, clarity and color as per standard protocol. The collected sample is washed several times with a washing medium under aseptic conditions. Unwanted debris and adipose (fat) layer is removed after the centrifugation at 1700 rpm for time duration of 7 minutes by suction. The lyses of red blood cells are allowed and nucleated marrow cells are separated.

After which the separated nucleated marrow cells are washed with DMEM culture medium (Dulbecco's Modified Eagle's Medium) and filtered through 40-μ filter to remove the debris. The cells are counted by using a hemocytometer. The homogenous cell suspension is seeded in tissue culture flasks along with culture medium.

Differentiation of osteo-progenitor cells in to osteoblasts, which is a 3-5-day process, is the ensuing process. In ideal conditions, after two days of culture, spent medium is removed and fresh differentiation medium is added for the differentiation of osteo-progenitor cells in to osteoblasts. Osteoblasts play the pivotal role of inducing the formation of the trabecular bone, which is a type of osseous tissue that in turn forms the bones.

The third sub-step following the differentiation procedure is the expansion of the osteoblasts in to an osteoblast growth culture, which requires approximately more than forty days starting from the initial day of isolation.

In this step, the culture flasks are transferred to a $CO_2$ incubator tuned to specific conditions, the temperature range being 37-38 degrees Celsius. The other conditions are maintained at 5% $CO_2$ and 80% humidified atmosphere. Furthermore, the culture flasks get replenished with fresh culture medium at regular intervals. In such cases, the average interval taken is two to three days. It is ensured that the cultured flasks are regularly inspected.

When the cultures reach confluence, the cells are dissociated from the flask surface and sub-cultured in fresh tissue culture flasks until the appropriate number (not less than 48 million cells) of expanded cells has been reached, thereby repeating the process till the culture is expanded in terms of the required number of cells. Quality control checks are an essential practice in laboratory methods and therefore the spent medium is pooled from every flask and sampled for sterility and mycoplasma tests. Mycoplasma tests are performed using the PCR method. Cell Characterization is performed by flow cytometry test checking bone alkaline phosphatase and collagen type I (CD 44$^+$ and/or 151$^+$) positive molecular markers, which are the basic criteria to study the cell surface expression. Here, Bone Alkaline Phosphatase and Collagen Type I (CD 44$^+$ and/or 151$^+$) are osteoblast cell surface markers, which are used to characterize cultured cells obtained at various stages. This test is followed by an Alizarin red stain test, which is performed to check the calcium deposition induced by these cells to confirm they are osteoblast in nature.

After the desired completion of expansion in to the osteoblast growth culture, the cells are detached and collected. The collected cells are centrifuged at 1400 rpm at an ambient temperature of 22-28 degree Celsius for about five-six minutes and washed with DMEM (Dulbecco's Modified Eagle's Medium) thoroughly. The cells obtained at the end of this stage are considered the active substance, which is the substance to be injected at the site of induction of bone.

In order to transport the active substance to the site where the bone needs to be induced, the harvested cells are filled in sterile vials and sealed effectively under aseptic conditions. The temperature to be maintained while transporting the same should be in the range of 2-8 degrees Celsius.

The active substance should be used within 72 hours from the date of manufacture of the same. In addition, the active substance should be allowed to settle down and solidify for 7-8 min before wound suture for effective regeneration of the defective bone.

Advantageously, it has been observed that on completion of ninety days, there is approximately ninety percent of bone regeneration while the conventional bone grafting is able to achieve sixty-five percent of bone regeneration.

Therefore by way of example as mentioned above the present invention has considerable advantages over conventional bone grafts and addresses the issues existing in the prior art.

EXAMPLES

Example 1: Avascular Necrosis

28 Years Male case study represents bilateral avascular necrosis i.e. defect in left and right hip joints of the femoral head. In the radiological report, FIG. 1, black color denotes the defect of bone due to necrosis. Ex-vivo cultured osteoblasts were injected to this patient in both the hip joints and after 90 days bone formation was observed in the radiological report, white color indicates bone regeneration.

Example 2: Avascular Necrosis

Figure 2:
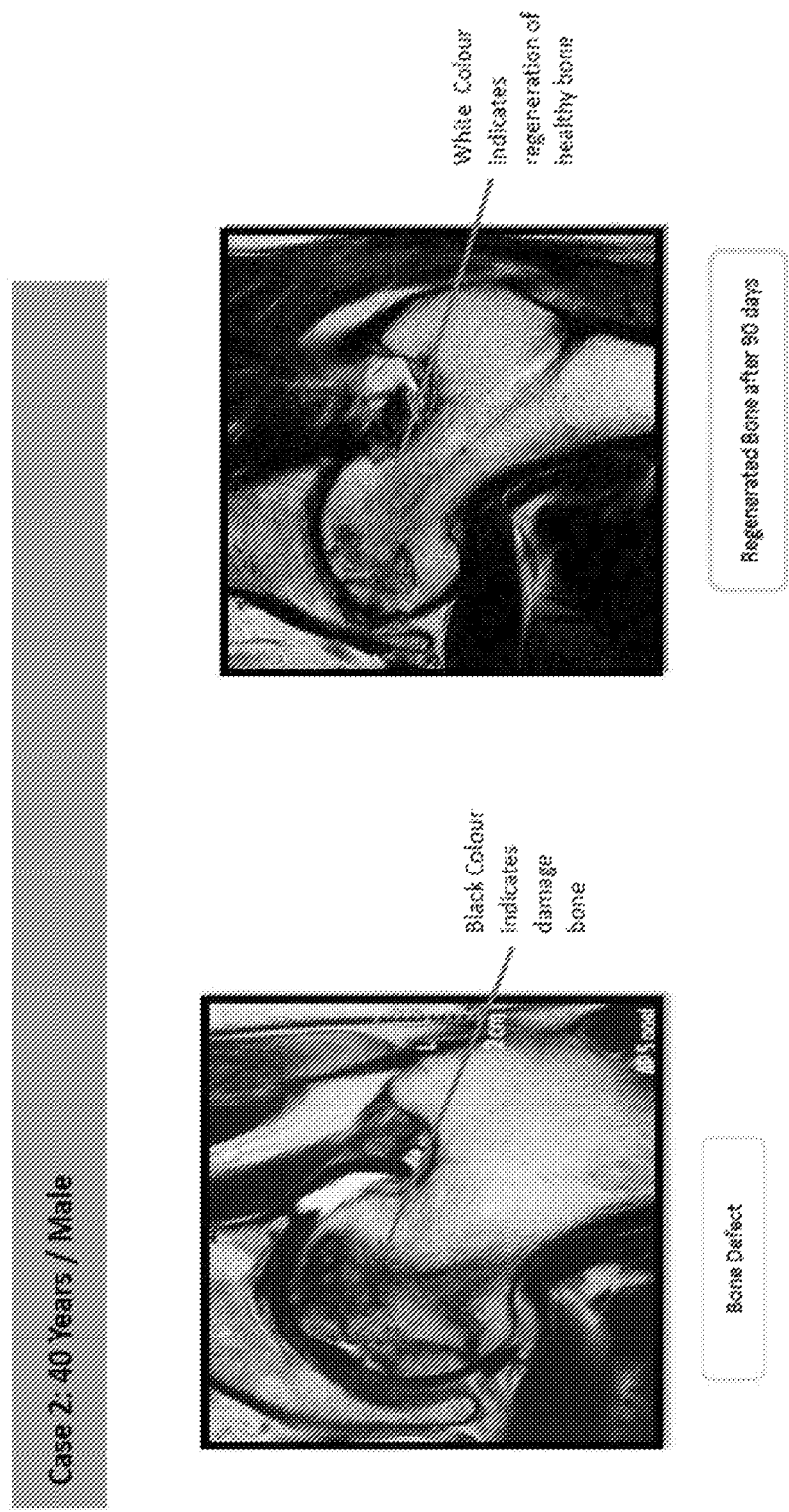
FIG. 2 is a radiological report wherein bone formation was observed 90 days after ex-vivo cultured osteoblasts were injected in a 40 year old patient in the left hip joint.

40 Years Male case study represents unilateral left hip avascular necrosis wherein black color indicates the defect of bone due to necrosis. Ex-vivo cultured osteoblasts were injected to this patient in the left hip joint and after 90 days bone formation was observed in the radiological report, FIG. 2, white color indicates bone regeneration.

Example 3: Avascular Necrosis

Figure 3:
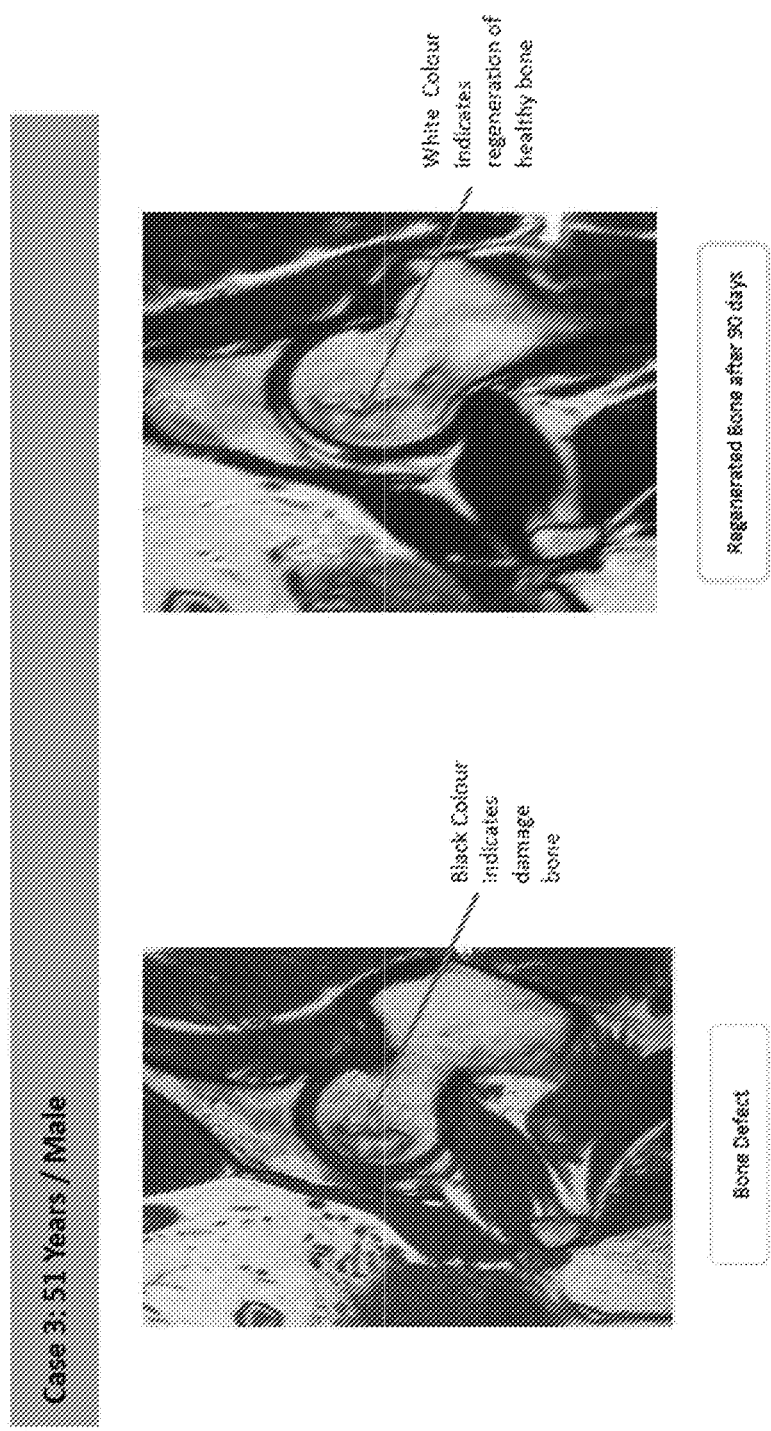
FIG. 3 is a radiological report wherein bone formation was observed 90 days after ex-vivo cultured osteoblasts were injected in a 51 year old patient in the left hip joint.

51 Years Male case study represents unilateral left hip avascular necrosis wherein black color indicates the defect of bone due to necrosis. Ex-vivo cultured osteoblasts were injected to this patient in the left hip joint and after 90 days bone formation was observed in the radiological report, FIG. 3, white color indicates bone regeneration.

Example 4: Oral and Maxillofacial Defects

Figure 4:
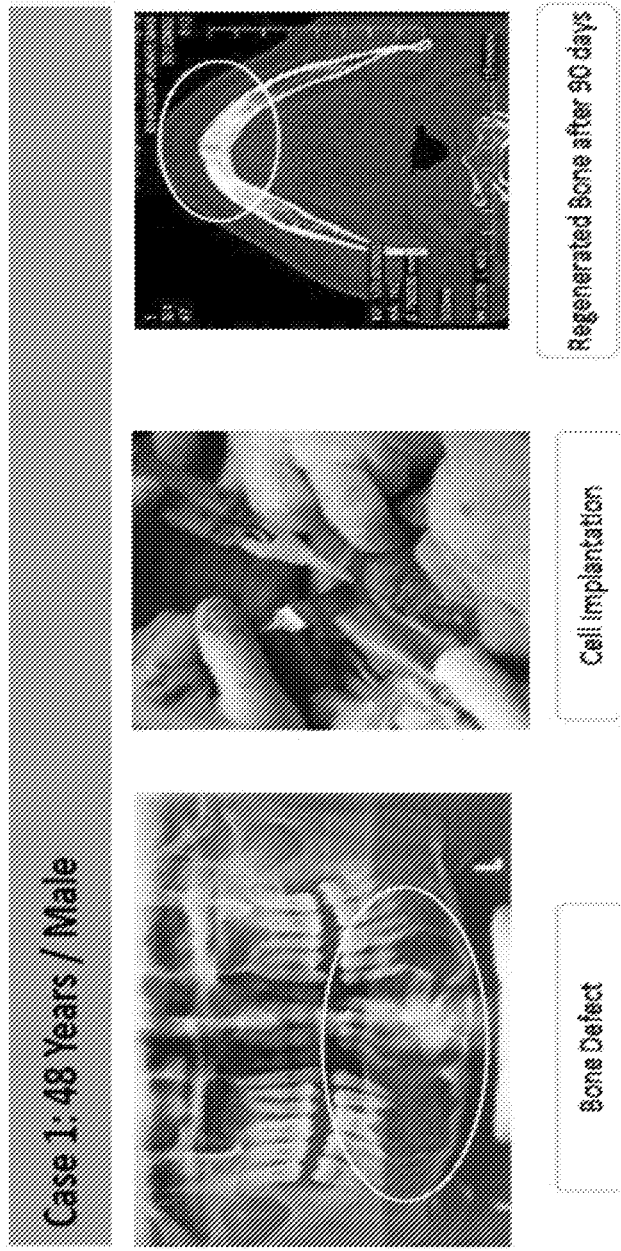
FIG. 4 is a radiological report wherein bone formation was observed 90 days after ex-vivo cultured osteoblasts were injected with the help of duploject in a 48 year old patient in the defect area of jaw.

48 Years Male case study represents oral and maxillofacial bone defect, wherein black color indicates the defect of jaw bone. Ex-vivo cultured osteoblasts were injected with the help of duploject to this patient in the defect area of jaw and after 90 days bone formation was observed in the radiological report, FIG. 4, white color indicates bone regeneration.

Example 5: Oral and Maxillofacial Defects

Figure 5:
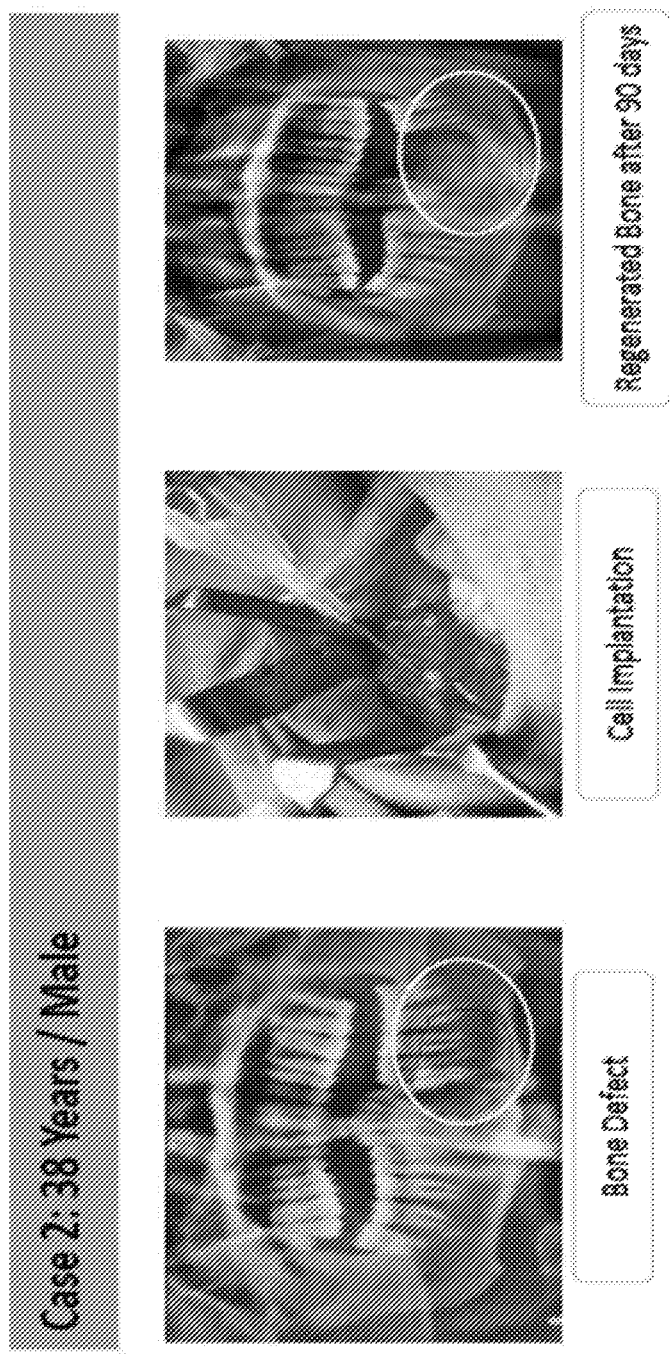
FIG. 5 is a radiological report wherein bone formation was observed 90 days after ex-vivo cultured osteoblasts were injected with the help of duploject in a 38 year old patient in the defect area of jaw.

38 Years Male case study represents oral and maxillofacial bone defect, wherein black color indicates the defect of jaw bone. Ex-vivo cultured osteoblasts were injected with the help of duploject to this patient in the defect area of jaw and after 90 days bone formation was observed in the radiological report, FIG. 5, white color indicates bone regeneration.

Example 6: Limb Lengthening

Figure 6:
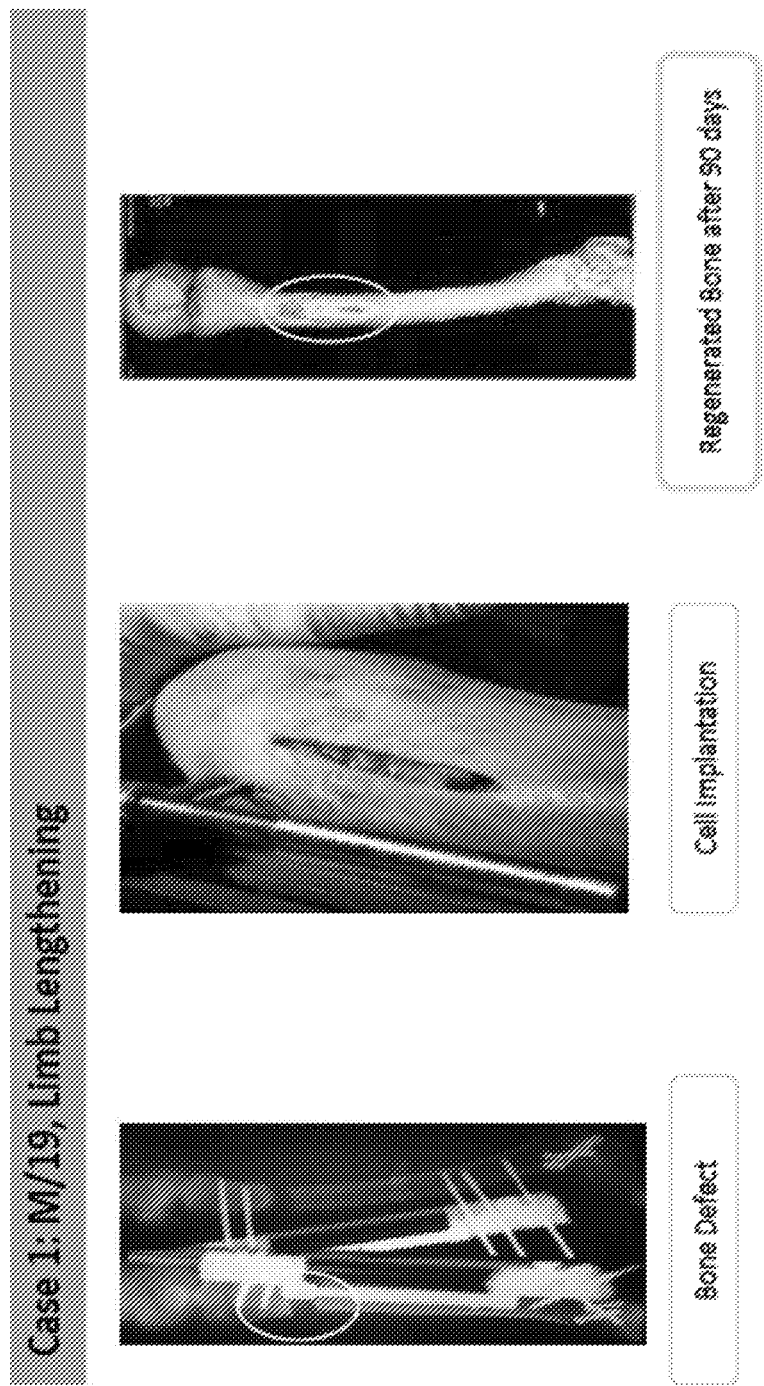
FIG. 6 is a radiological report wherein bone formation was observed 90 days after ex-vivo cultured osteoblasts were injected to a 19 year old patient in gap created on the limb.

19 Years Male case study represents increase in the size of limb this procedure known as limb lengthening, a gap is created and fixtures are applied. Ex-vivo cultured osteoblasts were injected to this patient in gap created on the limb and after 90 days bone formation was observed in the radiological report, FIG. 6, white color indicates bone regeneration.

Example 7: Fibrous Dysplasia

Figure 7:
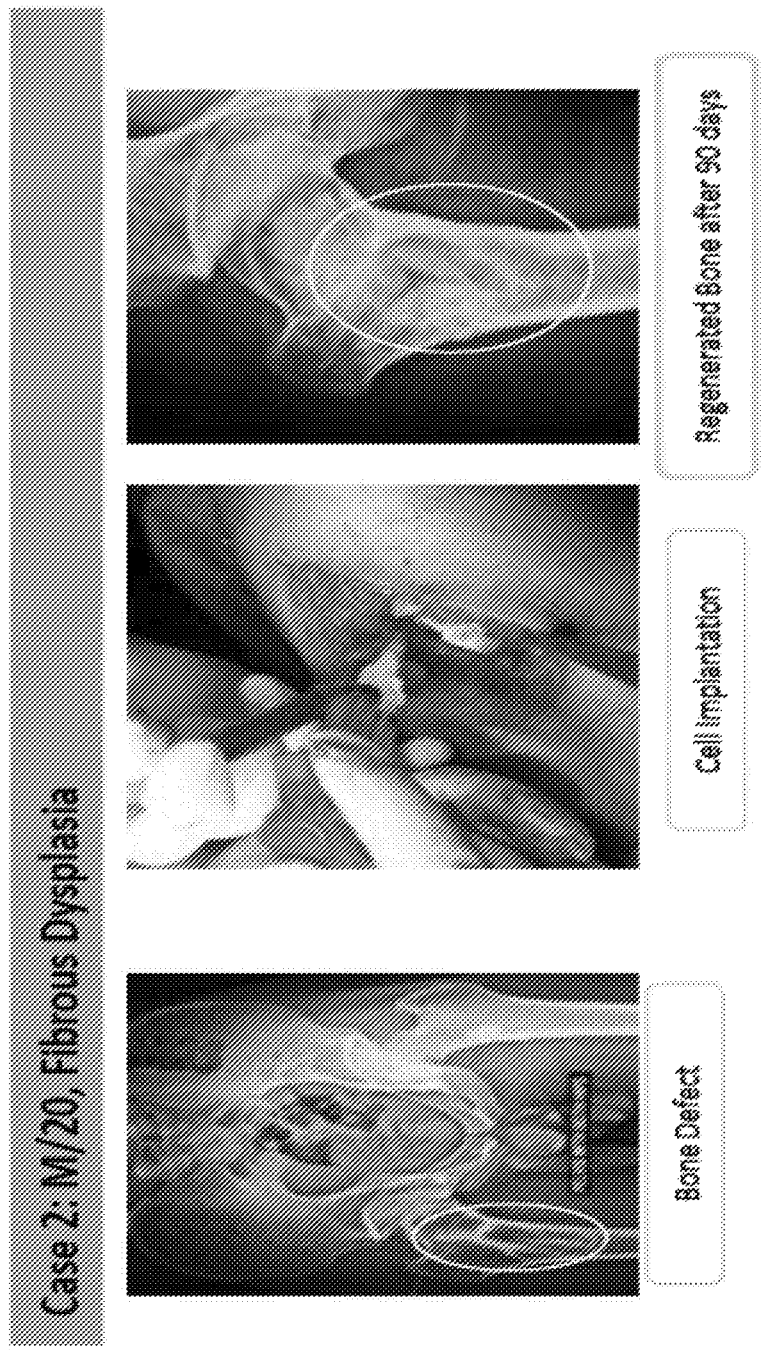
FIG. 7 is a radiological report wherein bone formation was observed 90 days after ex-vivo cultured osteoblasts were injected with duploject to a 20 year old patient in defect area of the femur bone.
Figure 8B:
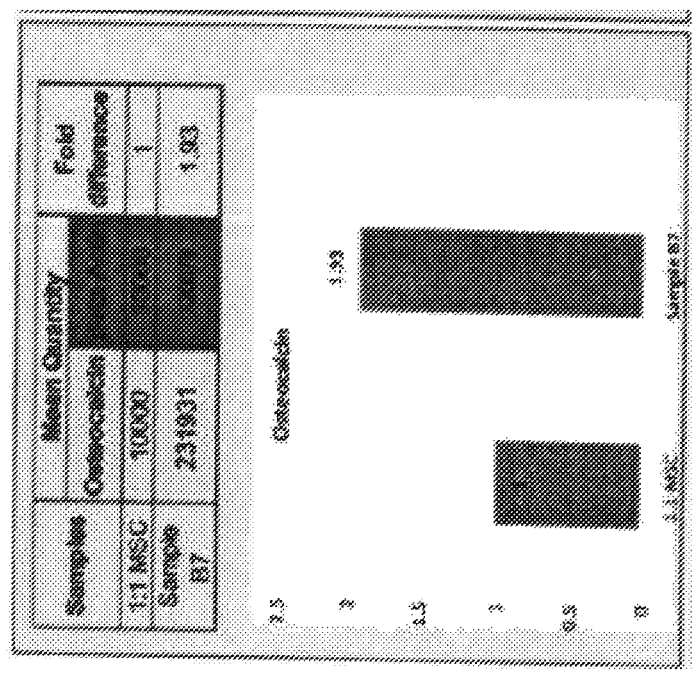
FIG. 8B shows the characterized of ex-vivo cultured osteoblasts cell (Sample B7) for gene expression studies by using RT PCR studies for Osteopontin.
Figure 8A:
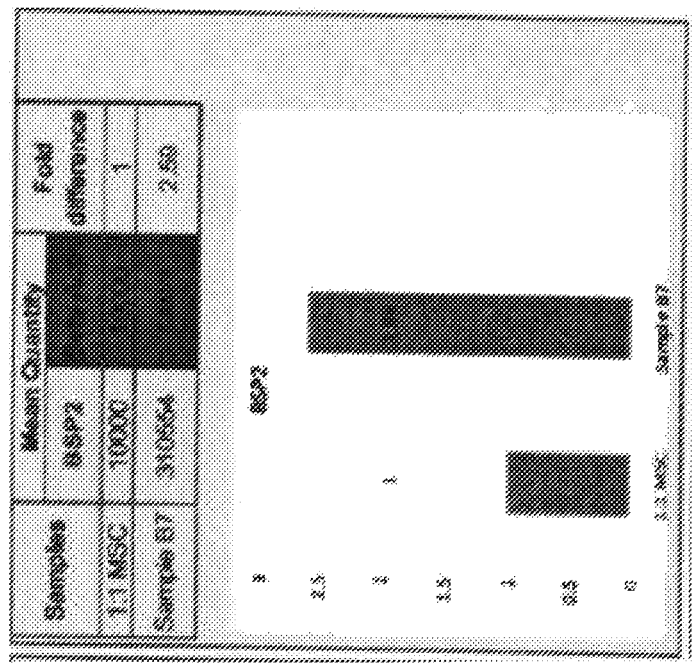
FIG. 8A shows the characterized of ex-vivo cultured osteoblasts cell (Sample B7) for gene expression studies by using RT PCR studies for Osteonectin.
Figure 8D:
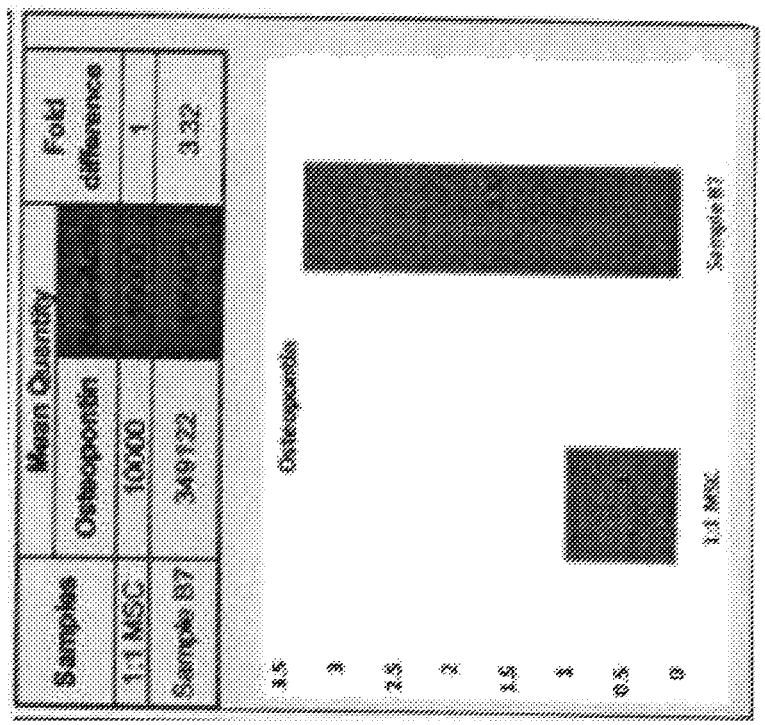
FIG. 8D shows the characterized of ex-vivo cultured osteoblasts cell (Sample B7) for gene expression studies by using RT PCR studies for Bone Sialo Protein II.
Figure 8C:
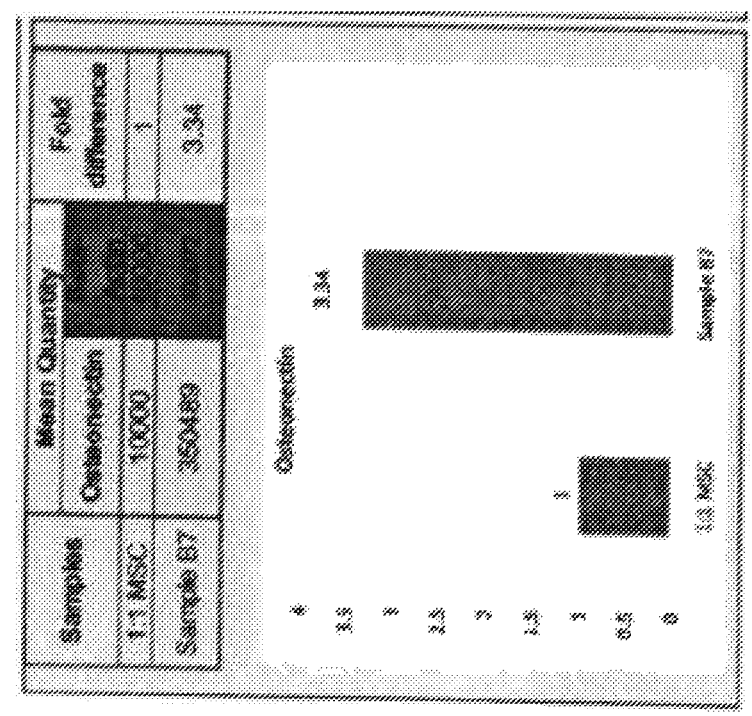
FIG. 8C shows the characterized of ex-vivo cultured osteoblasts cell (Sample B7) for gene expression studies by using RT PCR studies for Osteocalcin.

20 Years Male case study represents fibrous dysplasia where scar-like (fibrous) tissue has been developed in the femur (thigh) bone. Ex-vivo cultured osteoblasts were injected with duploject to this patient in the defect area of the femur bone after 90 days bone formation was observed in the radiological report, FIG. 7, white color indicates bone regeneration.

Example 8: RT PCR Data

Ex-vivo cultured osteoblasts cell (Sample B7) were characterized for gene expression studies by using RT PCR studies for Osteonectin, Osteopontin, Osteocalcin and Bone Sialo Protein II gene markers which are specific for Osteoblasts. In these studies, it has clearly shown (see FIGS. 8A, 8B, 8C and 8D) that all the four genes studied are showing positive expression compared with housekeeping gene β actin. The same studies reflects that osteoblasts are expressing all four genes more predominantly when compared with mesenchymal stem cells (MSC).

Example 9: FACS Results

Flow Cytometry Results (FACS) for Ex-Vivo Cultured Osteoblasts

Ex-vivo cultured osteoblast samples (OS-VL-10, OS-VL, 09 & OS-VL-08) were checked for characterization for cell surface markers Bone Alkaline phosphatase, Collagen type I (CD151$^+$) and CD105$^-$. This study showed that there is no impurity in the ex vivo cultured osteoblasts, as per the results mentioned in the table there is more than 98% expression of positive markers i.e. Bone Alkaline phosphatase, Collagen type I (CD151$^+$) and at the same time negative marker expression i.e. CD105$^-$ is very minimal about 2%, which indicates there is no impurity and confirms the presence of pure osteoblast cells. Please see Table 1 below.

TABLE 1

| | | | Positive Control | | Negative |
|---|---|---|---|---|---|
| No. | Sample ID | Stage | % Bone ALP | % Anti Collagen Type I (CD151*) | Control % CD105 |
| 1 | OS-VL-10 | FP | 92.53 | 99.86 | 0.36 |

| | | | Positive Control | | Negative |
|---|---|---|---|---|---|
| No. | Sample ID | Stage | % Bone ALP | % Anti Collagen Type I (CD151*) | Control % CD105 |
| 1 | OS-VL-09 | FP | 99.83 | 98.29 | 0.60 |

| | | | Positive Control | | Negative |
|---|---|---|---|---|---|
| No. | Sample ID | Stage | % Bone ALP | % Anti Collagen Type I (CD151*) | Control % CD105 |
| 1 | OS-VL-08 | FP | 93.24 | 99.56 | 2.11 |

I claim:
1. A method of inducing bone formation by ex-vivo osteoblast culturing for implantation, comprising:
   a) isolating osteo-progenitor cells from a harvest of a subject;
   b) differentiating the osteo-progenitor cells in to osteoblasts;
   c) expanding the osteoblasts for proliferation into an ex-vivo osteoblast growth culture;
   d) harvesting and washing the ex-vivo osteoblast growth culture;
   e) sub-culturing the ex-vivo osteoblast growth culture until the ex-vivo osteoblast growth culture reaches not less than 48 million cells to obtain an ex-vivo osteoblast culture;
   f) selecting an ex-vivo osteoblast culture for implantation from the characterized ex-vivo osteoblast culture by flow cytometry (FACS) with CD44+, CD151+, and CD105− expression markers;

g) collecting the selected ex-vivo osteoblast culture in Dulbecco's Modified Eagle's Medium (DMEM) to obtain an ex-vivo osteoblast culture for implantation; and h) injecting the collected ex-vivo osteoblast culture for implantation into a subject and examining bone formation and regeneration.

2. The method as claimed in claim 1, wherein the harvest of a subject is from a posterior-superior iliac crest or sternum.

3. The method as claimed in claim 1, wherein the isolating of osteo-progenitor cells includes separating of nucleated bone marrow cells.

4. The method as claimed in claim 3, wherein the separating of nucleated bone marrow cells is followed by washing of the nucleated bone marrow cells with DMEM culture medium.

5. The method as claimed in claim 1, wherein the differentiating the osteo-progenitor cells includes replenishing of differentiation medium in culture flasks.

6. The method as claimed in claim 1, wherein the expanding the osteoblasts further includes transferring of culture flasks to a $CO_2$ incubator at a temperature range of 37-38 degree Celsius.

7. The method as claimed in claim 6, wherein the $CO_2$ incubator is conditioned at a range of 5% $CO_2$ content.

8. The method as claimed in claim 6, wherein the $CO_2$ incubator is humidified at 80%.

9. The method as claimed in claim 1, wherein the harvesting step further includes centrifuging the ex vivo osteoblast growth culture or the ex-vivo osteoblast culture at a range of 1300-1500 rpm for five-six minutes.

10. The method as claimed in claim 9, wherein the centrifuging is followed by washing of the ex-vivo osteoblast growth culture or the ex-vivo osteoblast culture with DMEM.

11. The method as claimed in claim 1, wherein the ex-vivo osteoblast culture for implantation are filled in sterile vials, sealed effectively under aseptic conditions, transported at 2 to 8 degrees Celsius and used as active substance within 72 hours from date of manufacture.

12. The method as claimed in claim 1 further wherein the bone formation and regeneration at the site of induction of bone formation post implantation exhibits approximately ninety percent of bone regeneration on completion of ninety days.

* * * * *